United States Patent
Hochmair (10) Patent No.: US 10,953,232 B2
(45) Date of Patent: Mar. 23, 2021

(54) TELEMETRY OF IMPLANTED ELECTRODE CONTACTS DURING MRI

(71) Applicant: MED-EL Elektromedizinische Geraete GmbH, Innsbruck (AT)

(72) Inventor: Erwin Hochmair, Axams (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 147 days.

(21) Appl. No.: 15/742,574

(22) PCT Filed: Jul. 6, 2016

(86) PCT No.: PCT/US2016/041024
§ 371 (c)(1),
(2) Date: Jan. 8, 2018

(87) PCT Pub. No.: WO2017/007780
PCT Pub. Date: Jan. 12, 2017

(65) Prior Publication Data
US 2018/0353761 A1    Dec. 13, 2018

Related U.S. Application Data

(60) Provisional application No. 62/190,305, filed on Jul. 9, 2015.

(51) Int. Cl.
*A61N 1/37* (2006.01)
*A61N 1/372* (2006.01)
(Continued)

(52) U.S. Cl.
CPC .......... *A61N 1/3718* (2013.01); *A61B 5/0008* (2013.01); *A61B 5/0017* (2013.01);
(Continued)

(58) Field of Classification Search
CPC .. A61N 1/0541; A61N 1/3718; A61N 1/3727; A61N 1/36038; A61B 5/0008;
(Continued)

(56) References Cited

U.S. PATENT DOCUMENTS 8,570,040 B2    10/2013   Leigh et al.
2006/0025820 A1*  2/2006  Phillips .................. A61B 5/055
                                                                607/2
(Continued)

FOREIGN PATENT DOCUMENTS

CN    101801454 A    8/2010
CN    102576059 A    7/2012

OTHER PUBLICATIONS

International Searching Authority, International Search Report and Written Opinion, International Application No. PCT/US2016/041024, 18 pages, dated Sep. 14, 2016.
(Continued)

*Primary Examiner* — Christopher A Flory
(74) *Attorney, Agent, or Firm* — Sunstein LLP (57) ABSTRACT

A magnetic resonance imaging (MRI) telemetry arrangement and process for a cochlear implant system are described. Electrode current is measured that is induced in a cochlear implant electrode lead during an MRI process performed on an implanted patient. An MRI telemetry signal for an external telemetry sensor is then output based on the measured electrode current.

17 Claims, 5 Drawing Sheets

(51) Int. Cl.

| | |
|---|---|
| *A61B 5/01* | (2006.01) |
| *A61B 5/055* | (2006.01) |
| *A61N 1/05* | (2006.01) |
| *A61B 5/00* | (2006.01) |
| *G01R 33/28* | (2006.01) |
| *A61B 5/12* | (2006.01) |
| *A61N 1/36* | (2006.01) |

(52) U.S. Cl.
CPC .............. *A61B 5/0031* (2013.01); *A61B 5/01* (2013.01); *A61B 5/055* (2013.01); *A61B 5/12* (2013.01); *A61B 5/686* (2013.01); *A61B 5/6817* (2013.01); *A61N 1/0541* (2013.01); *A61N 1/36038* (2017.08); *A61N 1/3727* (2013.01); *G01R 33/288* (2013.01); *A61B 5/002* (2013.01); *A61B 5/6815* (2013.01); *A61B 5/6877* (2013.01); *A61B 5/7225* (2013.01); *A61B 2560/0209* (2013.01); *A61B 2560/0219* (2013.01); *A61B 2560/0223* (2013.01)

(58) Field of Classification Search
CPC ..... A61B 5/0017; A61B 5/0031; A61B 5/002; A61B 5/01; A61B 5/055; A61B 5/12; A61B 5/6815; A61B 5/6817; A61B 5/686; A61B 5/6877; A61B 5/7225; G01R 33/288
See application file for complete search history.

(56) References Cited

U.S. PATENT DOCUMENTS

| | | | |
|---|---|---|---|
| 2010/0023000 A1 | 1/2010 | Stevenson et al. | |
| 2011/0112599 A1 | 5/2011 | Zhang et al. | |
| 2011/0160806 A1 | 6/2011 | Lyden et al. | |
| 2011/0160808 A1* | 6/2011 | Lyden ...................... | A61N 1/37 607/63 |
| 2011/0213445 A1* | 9/2011 | Blischak .............. | A61N 1/0553 607/72 |
| 2011/0270362 A1 | 11/2011 | Goedeke et al. | |
| 2012/0035698 A1 | 2/2012 | Johnson et al. | |
| 2012/0158095 A1 | 6/2012 | Jolly | |
| 2012/0226140 A1 | 9/2012 | Min et al. | |
| 2013/0090707 A1 | 4/2013 | Doerr et al. | |
| 2014/0288619 A1* | 9/2014 | Johnson ................... | A61N 1/05 607/60 |
| 2014/0296699 A1 | 10/2014 | Stessman et al. | |
| 2014/0330357 A1* | 11/2014 | Stevenson ................ | A61N 1/05 607/116 |
| 2014/0378820 A1* | 12/2014 | Gururaj .................. | A61B 5/055 600/411 |
| 2015/0207484 A1* | 7/2015 | Stevenson ................ | A61N 1/05 333/206 |
| 2016/0067497 A1* | 3/2016 | Levine .................. | A61B 5/4836 607/62 |
| 2016/0144183 A1* | 5/2016 | Marnfeldt .......... | A61N 1/36125 607/63 |
| 2016/0144184 A1* | 5/2016 | Marnfeldt .......... | A61N 1/36125 607/63 |

OTHER PUBLICATIONS

Lazeyras et al., "Functional MRI of Auditory Cortex Activated by Multisite Electrical Stimulation of the Cochlea," NeuroImage 17, pp. 1010-1017, 2002.
Ballweg et al., "RF tissue-heating near metallic implants during magnetic resonance examinations: an approach in the ac limit," Medical Physics, 38 (10), pp. 5522-5529, Oct. 2011 (Abstract only).
Acikel et al., "Modeling of radio-frequency induced currents on lead wires during MR imaging using a modified transmission line method," Medical Physics, 38 (12), pp. 6623-6632, Nov. 2011.
European Patent Office, Supplementary European Search Report, Application No. 16821884.0-1115, 12 pages, dated May 25, 2018.
China National Intellectual Property Administration, Office Action, Application No. 201680039689.6, dated Dec. 30, 2019, 9 pages.
China National Intellectual Property Administration, Office Action, Application No. 201680039689.6, dated Sep. 4, 2020, with English translation, 22 pages.

* cited by examiner

TELEMETRY OF IMPLANTED ELECTRODE CONTACTS DURING MRI

This application is a National Phase Entry of Patent Cooperation Treaty Application PCT/US2016/041024, filed Jul. 6, 2016, which in turn claims priority from U.S. Provisional Patent Application 62/190,305, filed Jul. 9, 2015, which is incorporated herein by reference in its entirety.

FIELD OF THE INVENTION

The present invention relates to implantable neural prosthesis such as cochlear and vestibular implant systems, and specifically, increasing the safety of such devices for use with Magnetic Resonance Imaging (MRI).

BACKGROUND ART

Figure 1:
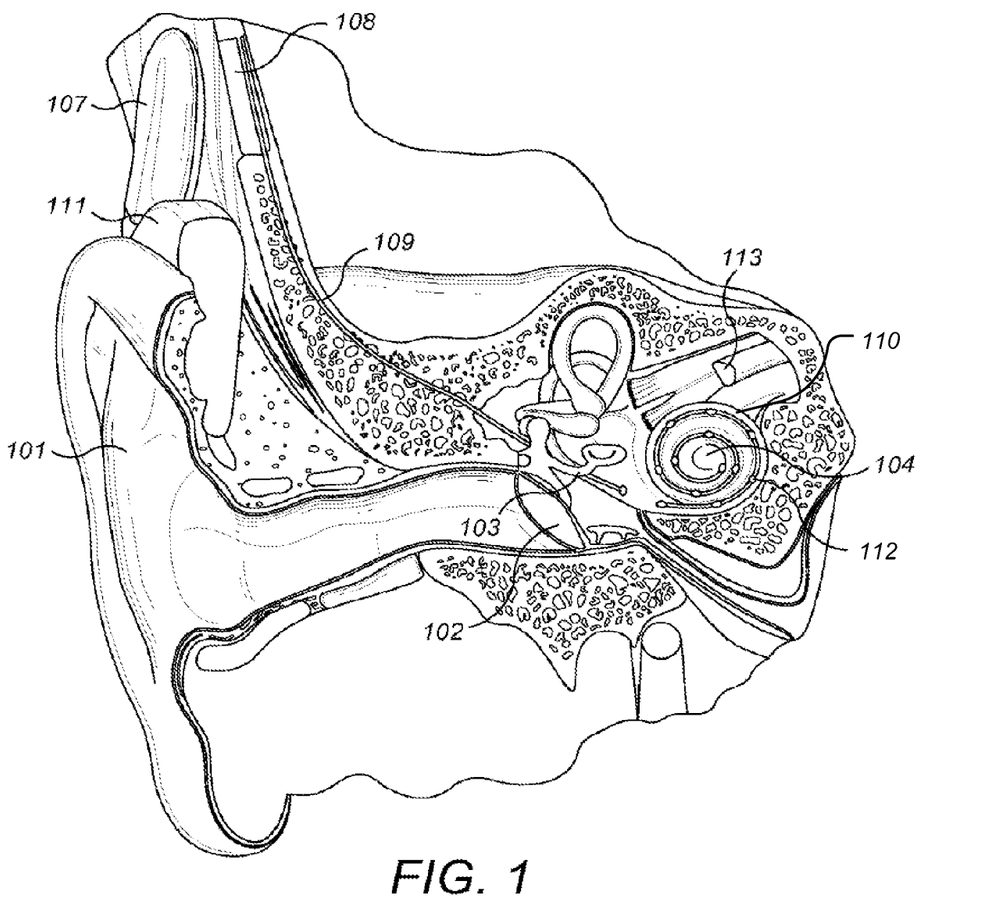
FIG. 1 shows the anatomy of a human ear and some components of a typical cochlear implant system.

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the auditory nerve 113 reside. In response to received sounds transmitted by the middle ear 103, the fluid filled cochlea 104 functions as a transducer to generate electric pulses that are transmitted to the auditory nerve 113, and ultimately to the brain. Hearing is impaired when there are problems in the ability to transduce external sounds into meaningful action potentials along the neural substrate of the cochlea 104.

In some cases, hearing impairment can be addressed by an auditory prosthesis system such as a cochlear implant that electrically stimulates auditory nerve tissue with small currents delivered by multiple stimulation contacts distributed along an implant electrode. FIG. 1 shows some components of a typical cochlear implant system where an external microphone provides an audio signal input to an external signal processing stage 111 which implements one of various known signal processing schemes. The processed signal is converted by the external signal processing stage 111 into a digital data format, such as a sequence of data frames, for transmission into a receiver processor in an implant housing 108. Besides extracting the audio information, the receiver processor in the implant housing 108 may perform additional signal processing such as error correction, pulse formation, etc., and produces a stimulation pattern (based on the extracted audio information) that is sent through an electrode lead 109 to an implanted electrode array 110 which penetrates into the cochlea 104 through a surgical opening in the outer surface of the cochlea 104. Typically, this electrode array 110 includes multiple stimulation contacts 112 on its surface that deliver the stimulation signals to adjacent neural tissue of the cochlea 104 which the brain of the patient interprets as sound. The individual stimulation contacts 112 may be activated sequentially, or simultaneously in one or more contact groups.

The widely used technique of Magnetic Resonance Imaging (MRI) can pose various risks for patients with implantable electronic devices such as for example cochlear or vestibular implant systems. For example, in implants with elongated electrode leads containing at least one electrode wire having a terminal end forming an electrode contact, interactions with the induced RF pulses can lead to MRI-induced tissue heating near the elongated electrode leads and in particular adjacent the electrode contacts. At best, this may be just uncomfortable for the patient. At worst, such unintentional MRI-induced electrode lead currents may be dissipated within the tissue adjacent to the electrode contacts and thereby may overheat and damage this tissue. MRI-induced currents also can result in unintentional stimulation of the target neural tissue. This is particularly the case for cochlear and vestibular implants, because device design makes non-linear elements coupled to the at least one wire contained within the elongated electrode lead at the implant housing side necessary. Such non-linear elements may rectify the MRI-induced current that subsequently may unintentionally stimulate target neural tissue (e.g. with cochlear implants there may be unintentional auditory sensations during MRI).

Currently, MRI-related tissue heating caused by MRI-induced electrode lead currents, and in general within electrically conductive elongated implant structures, is avoided by having a prohibition against the use of MRI on patients having such implants. This may be either a complete prohibition against MRI, or a partial limit that permits only low-field MRI and/or low Specific Absorption Rate (SAR) values. Alternatively or in addition, electrode wire coiling may be used to improve safety with MRI. Such alternative solutions have proven to be less effective and/or may consume considerable space.

The strength of MRI-induced current effects depends on multiple factors such as electrode lead length, electrode contact size, MRI equipment/scanner, and MRI sequences used. Even MRI scanners using the same magnetic field strength may generate widely different local RF fields. The impedance, inductance and capacitance of the electrode circuit and the stimulator housing also have a significant influence on the strength of these effects. Due to the many different factors that are involved, no generally valid relationship can be established between SAR values, the RF-magnetic field, and the RF-electric field that is responsible for the induction of the MRI-induced current in the at least one wire contained in the elongated electrode lead.

In some cases additional temperature sensors can be incorporated into implantable electrode leads that can directly measure tissue or electrode contact or lead temperatures. But for implantable medical devices with thin implantable electrode leads that are placed close to heat sensitive target neural tissue, it is not feasible to add or embed such temperature sensors within or close to the electrode lead, because of the overriding requirements of flexibility and size and required temperature measurement accuracy. Such medical devices are for example cochlear and vestibular implants where the elongate electrode lead is inserted into the delicate structures of the scala tympani of the cochlear or vestibule of the vestibular system, respectively.

SUMMARY OF THE INVENTION

Embodiments of the present invention are directed to cochlear implant arrangements which include an implantable electrode lead having electrode wires that each have a terminal end that forms an electrode contact which is configured to deliver electrode stimulation signals carried by the electrode wires to adjacent auditory neural tissue for perception as sound by an implanted patient. An implantable stimulator is coupled to the electrode lead and configured to process an implant communications signal received from an external transmitter device to produce the electrode stimulation signals for the plurality of electrode wires. And a magnetic resonance imaging (MRI) telemetry module is coupled to the implantable stimulator and the electrode lead and configured to: i. measure electrode current induced in the electrode lead during an MRI process performed on the implanted patient, and ii. output an MRI telemetry signal for an external telemetry sensor based on the measured electrode current.

In specific embodiments, the MRI telemetry signal may typically represent a tissue temperature signal determined by the MRI telemetry module as a function of the measured electrode current to indicate tissue heating occurring at the electrode contacts from the MRI process. For example, the MRI telemetry signal may further reflect a frequency dependent relationship between the measured electrode current and the tissue heating.

There may be an MRI telemetry memory that is coupled to the MRI telemetry module and configured to receive the MRI telemetry signal output from the MRI telemetry module for later delivery to the external telemetry sensor after conclusion of the MRI process. And an MRI telemetry link may be configured to deliver the MRI telemetry signal from the MRI telemetry module to the external sensor during the MRI process; for example, via an optical link or a radiofrequency link.

The MRI telemetry module may be configured to measure electrode current on only one electrode wire, or one multiple electrode wires. There may be electrode driver amplifiers configured to deliver the stimulation signals to the electrode wires, in which case, the MRI telemetry module may be configured to measure electrode current based on a supply voltage generated for the electrode driver amplifiers during the MRI process.

DETAILED DESCRIPTION OF SPECIFIC EMBODIMENTS

Embodiments of the present invention are based on determining tissue heating caused by MRI induced electrode lead currents based on a functional relation between the MRI induced electrode lead current and the expected tissue heating adjacent to the electrode contact that can be supplied by the electrode manufacturer. This relation allows using a measurement of the electrode lead current during the MRI scan procedure to infer the tissue temperature adjacent to the electrode contract in situ in that particular configuration.

Figure 2A:
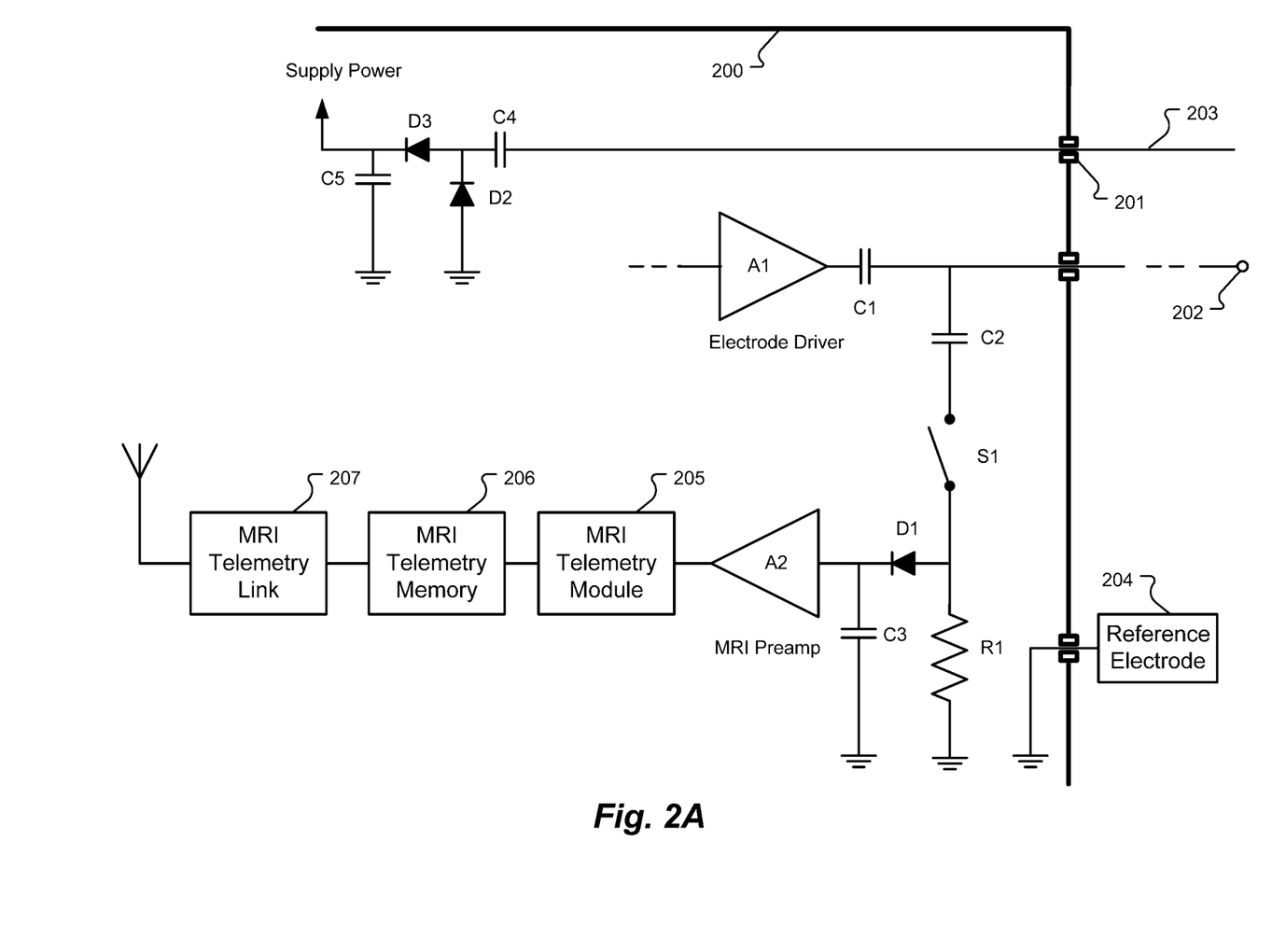
FIGS. 2A-2B show components in a cochlear implant having an MRI telemetry arrangement according to embodiments of the present invention.
Figure 2B:
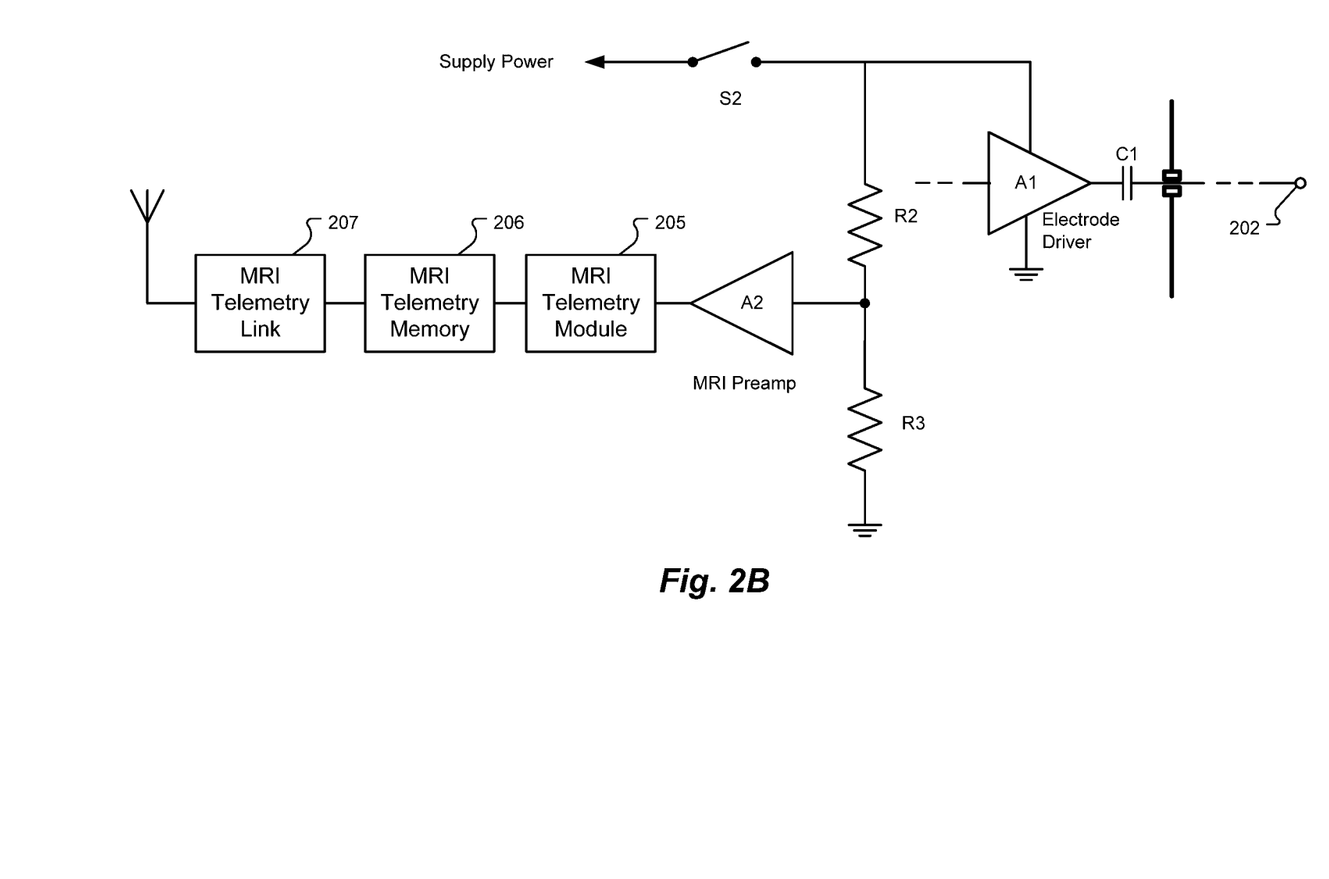

FIGS. 2A-2B show components of implantable neural prosthesis systems having an MRI telemetry arrangement according to embodiments of the present invention. An implantable stimulator housing 200, typically made of titanium, is hermetically sealed to protect the components within from the fluids in the surrounding bodily tissues when implanted. There are a limited number of through openings in the stimulator housing 200, sealed with an electrical insulator 201, that allow electrical wires to penetrate from the outside into the stimulator housing 200. It is typical but not necessary for implantable neural prosthesis to have a reference electrode 204 from unstimulated local tissue that penetrates into the stimulator housing 200 to complete the current path for the stimulation signals. An example of an implantable neural prosthesis system comprising a reference electrode 204 are cochlear or vestibular implant systems employing monopolar stimulation. In a typical cochlear implant system, one of those through connections is an electrode lead with multiple electrode wires that each have a terminal end that forms an electrode contact 202 which is located on the outer surface of a distal end electrode array portion of the electrode lead which is implanted within a patient cochlea and configured to deliver electrode stimulation signals carried by the electrode wires to adjacent auditory neural tissue for perception as sound by an implanted patient During normal (non-MRI) operation of the system, stimulation signal processing components within the stimulator housing 200 (mostly not shown) process an implant communications signal that is received transcutaneous, e.g. by a coil antenna, from an external transmitter device to produce the electrode stimulation signals, which ultimately are driven by an electrode driver A1 through signal coupling capacitor C1 to the electrode wires in the electrode lead. For a total implantable neural prosthesis, the stimulation signal processing components process a signal received from an implantable sensor, for example an implantable microphone for a cochlear implant or a gyroscope for a vestibular prosthesis, to produce the electrode stimulation signals. During an MRI process that is performed on the implanted patient, the power supply to the normal stimulator processing components is disabled, and optional switch S1 is closed to engage components in an MRI telemetry section. Optional switch S1 may be any known suitable element, such as for example and without limitation, an n-channel MOSFET with gate connected to drain that is closed automatically when the implant is not powered and may open automatically upon powering the implant or in addition upon applying a dedicated signal. The MRI telemetry components measure the electrode current that is induced in at least one wire in the electrode lead by the RF field, and based on the measured electrode current transmit a corresponding MRI telemetry signal to an external telemetry monitor.

More specifically, the MRI electrode current signal can be measured via C2 through optional switch S1, be rectified by R1/D1/C3, and amplified by MRI Preamp A2 for MRI Telemetry Module 205. The size of the measurement load resistor R1 and optional resistor R4 determines the dynamic range of the MRI electrode current measurement. For an implantable neural prosthesis with multiple channels, for example a multichannel cochlear implant, where each channel is associated with one wire in the electrode lead, various different current measurement schemes are possible:

Measure just one electrode channel (e.g., the electrode contact 202 nearest to the distal electrode tip where the RF field strength and MRI induced electrode current may be greatest)

Measure all or a subset of electrode channels sequentially over time, or

Measure all or a subset of the electrode channels simultaneously.

The implantable neural prosthesis may change upon request received from an external transmitter device, such as the telemetry monitor, or apply in timely alternating order the current measurement scheme. The used current measurement scheme may depend on the scheme specific standard deviation and/or highest scheme specific mean or maximum value of the measured MRI electrode current signal. The measurement scheme with the smallest scheme specific standard deviation and/or highest scheme specific mean or maximum value may be chosen. From all the measurements performed for the current measurement scheme being used, the measured induced MRI electrode current that is used for the subsequent steps, i.e. MRI electrode current signal, may be derived by either selecting the maximum or mean measurement among the measured channels. The maximum and mean measurement may be either over channels or time-frame or both.

This circuit can be further configured to perform simple frequency shaping to compensate for any frequency dependence of the relation between the induced MRI electrode current so as to make the MRI electrode current signal and hence the current/temperature relation independent of the MRI RF frequency. The RF-frequency of the MRI scanner varies in between 64 MHz for an MRI imaging at 1.5 Tesla magnetic field strength and 128 MHz for an MRI imaging at 3 Tesla magnetic field strength. Frequency dependence may be compensated for this RF-frequency range by adding capacitor C2 parallel to R1 and proper dimensioning. C2 has to be chosen sufficiently small in order not to bias the stimulation pulse, particularly when the optional switch S1 is omitted, typically in the range from 20-30 pF. The resistors R1 and R4 are chosen to fulfill for the impedances Z in the frequency range 64-128 MHz the following relation:

$$Z_{C2} << Z_{R4} + Z_{R1}$$

In a further step, the measured MRI electrode current signal may be converted into the estimated tissue temperature adjacent to the electrode contact by evaluating the following equation:

$$T_{tissue} = f(I_w, f_r, a)$$

Where $f$ may be a linear or non-linear function of the MRI electrode current signal $I_w$, frequency $f_r$ of the MRI RF-field and the calibration coefficients a determined during manufacturing. It is understood that additional dependencies may be included into the mapping without departing from the inventive concept. The calibration coefficients may be stored in the implantable neural prosthesis, the external telemetry monitor or may be accessible through a database. The calibration coefficients may be queried by the external telemetry monitor from the database with a unique serial number stored in the neural prosthesis. The database may be run on a central server in a network, such as for example the internet where the access may be secured and limited. There may be multiple sets of calibration coefficients, one for each used current measurement scheme. The calibration coefficients may further reflect the particular electrode lead properties, such as wire shape (straight, undulated), number of wires and their relative location within the electrode lead to each other and manufacturing tolerances. Further, the coefficients may be wire or subset of wire specific, e.g. pertaining to a particular wire with the electrode contact 202 nearest to the distal electrode tip. The calibration coefficients may define properties of function $f$, e.g. $f(x) = a_1 I_w + a_0$ or $f(x) = a_2 I_w^2 + a_0$ for linear and non-linear mappings respectively.

The calibration coefficients are determined during manufacturing as described in the following. The calibration procedure is explained on the basis of a multichannel cochlear implant in the following, but does apply to any other implantable neural prosthesis in the same way. A known manufacturing process for a cochlear electrode lead is for example described in U.S. Pat. No. 5,876,443 to Hochmair. After assembly of the electrode lead and connecting to the stimulator housing and coating with for example silicone, the cochlear implant is ready for final functional testing. During this test, the electrode lead may be inserted into a model of the cochlear, i.e. a spiral duct filled with saline solution as part of a model mimicking implantation in the skull of a patient. The implant may be exposed to an RF-field in the way the MRI scanner would produce and the induced current in the electrode wires are measured. Simultaneously, the temperature in vicinity to the electrode contracts may be measured with a contactless temperature measurement method, such as for example an infrared camera. The calibration coefficients are calculated from the measured current and the measured temperature. In one embodiment, the calibration coefficients may be calculated for each measurement scheme. Any state-of-the-art fitting algorithm may be used for this purpose.

In reference to FIG. 2A, the MRI Telemetry Module 205 is an analog-to-digital encoder that determines the MRI telemetry signal as a function of the measured electrode current (e.g., as a frequency dependent relationship) to represent temperature that occurs at the electrode lead or contacts 202 from the MRI process. The MRI Telemetry Module 205 outputs the MRI telemetry signal to MRI Telemetry Memory 206. The MRI Telemetry Memory 206 may store the MRI telemetry signal for later delivery by MRI Telemetry Link 207 to the external telemetry sensor after conclusion of the MRI session. For example, there may be an initial explorative pre-session at a lower MRI magnetic field strength that generates the MRI telemetry signal representing electrode lead or contact temperature, from which the MRI magnetic field strength limit could be extrapolated. The measurement scheme may be determined during such explorative pre-session with the criteria as set out above. Or MRI Telemetry Memory 206 can be used as output buffer that immediately provides the MRI telemetry signal for output by the MRI Telemetry Link 207 to the external telemetry sensor in real time during the MRI session. The MRI Telemetry Link 207 may be an optical link in which the stimulator housing 200 contains a Telemetry Link LED (preferably infrared) for the transcutaneous transmission to an externally applied optical receiver, such optical link being immune to interference from the RF-field of the MRI scanner. Or the MRI Telemetry Link 207 may be a radiofrequency link; for example one which transmits the MRI telemetry signal only during gaps between MRI pulses or during longer gaps between series of MRI pulses to avoid interference with the RF-field from the MRI scanner, and the external telemetry monitor could be synchronized accordingly.

To perform the MRI electrode current measurement in real time, the components in the MRI telemetry section need electrical power. This MRI component power may be obtained from an internal battery or a sufficiently large pre-charged capacitor. Or, as shown in FIG. 2A, the MRI supply power can be developed by harvesting electrical energy from the MRI RF field using an MRI power wire 203 that penetrates into the stimulator housing 200 and is rectified by the MRI power circuit C5/D2/D3/C6 to power (e.g. by using some extra wire extending from the implant) the MRI telemetry components. In an embodiment the electrical energy harvesting may be through the coil antenna of the MRI Telemetry Link. This has the advantage that no extra external components are required.

FIG. 2B shows an alternative embodiment where the MRI telemetry section components are configured to measure electrode current based on a supply voltage generated through the electrode driver amplifier A1 during the MRI process. In such arrangements, the MRI induced current during MRI in the wire coupled to the driver amplifier A1 will be rectified by the driver amplifier A1 due to its non-linear properties and supply voltage is generated. The generated supply voltage is an indication of the MRI electrode current. No extra rectification is necessary, which simplifies the necessary circuitry. This MRI voltage can also be used to power the MRI telemetry section components. In other embodiments, the voltage induced by the MRI magnetic field in the receiving coil of the cochlear implant may be used to develop the MRI supply voltage.

Figure 3A:
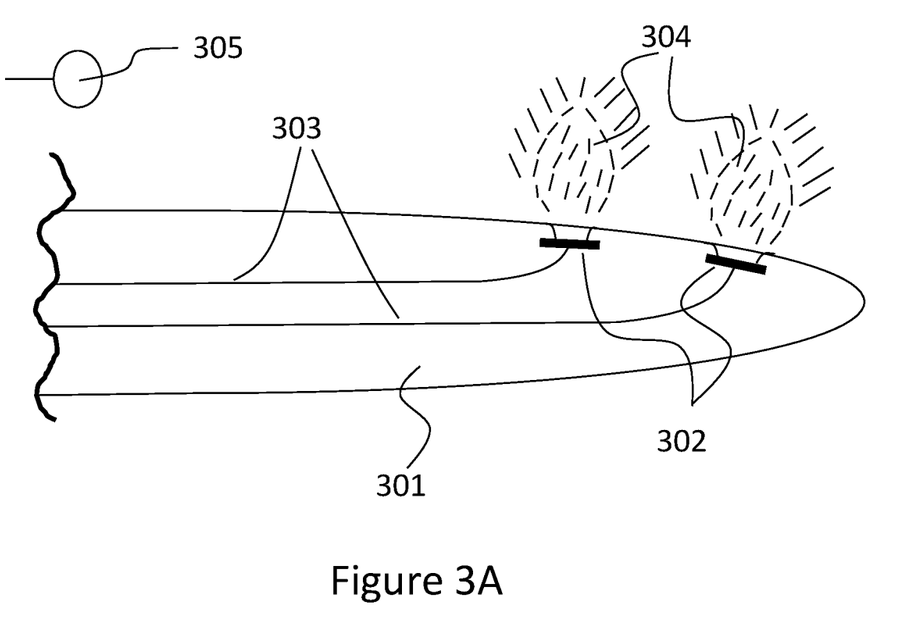
FIG. 3A-3B show an example electrode with multiple electrode contacts and an equivalent circuit diagram, respectively.

FIG. 3A shows an example electrode lead 301 comprising two electrode contacts 302, each being the terminal end for the electrode wire 303 that terminates in the stimulator housing as shown in FIG. 2A. Optionally a separate ground electrode 305 may be present. Although the electrode contacts 302 are made of biocompatible material, such as for example platinum, titanium or MP35N, inflammatory reaction of the body may lead to fibrous tissue 304 growth in the vicinity of the electrode contacts 302. During an MRI process, a current is induced by the RF-field of the MRI scanner in the electrode wires 303. The induced current will not terminate at the electrode contact 302, but will flow and spread out through the tissue 304 adjacent to the electrode contact 302. The current density and so the tissue heating reduce with distance from the electrode contact 302. The impedance of the electrode wire 303 and electrode contact 302 is typically in the range of some milliohms to ohms. The impedance of the fibrous tissue 304 is typically a magnitude higher in the range of some hundred ohms or some kilo ohms. Therefore the tissue 304 heats up mainly due to direct dissipation of the induced electric current in fibrous tissue 304.

Figure 3B:
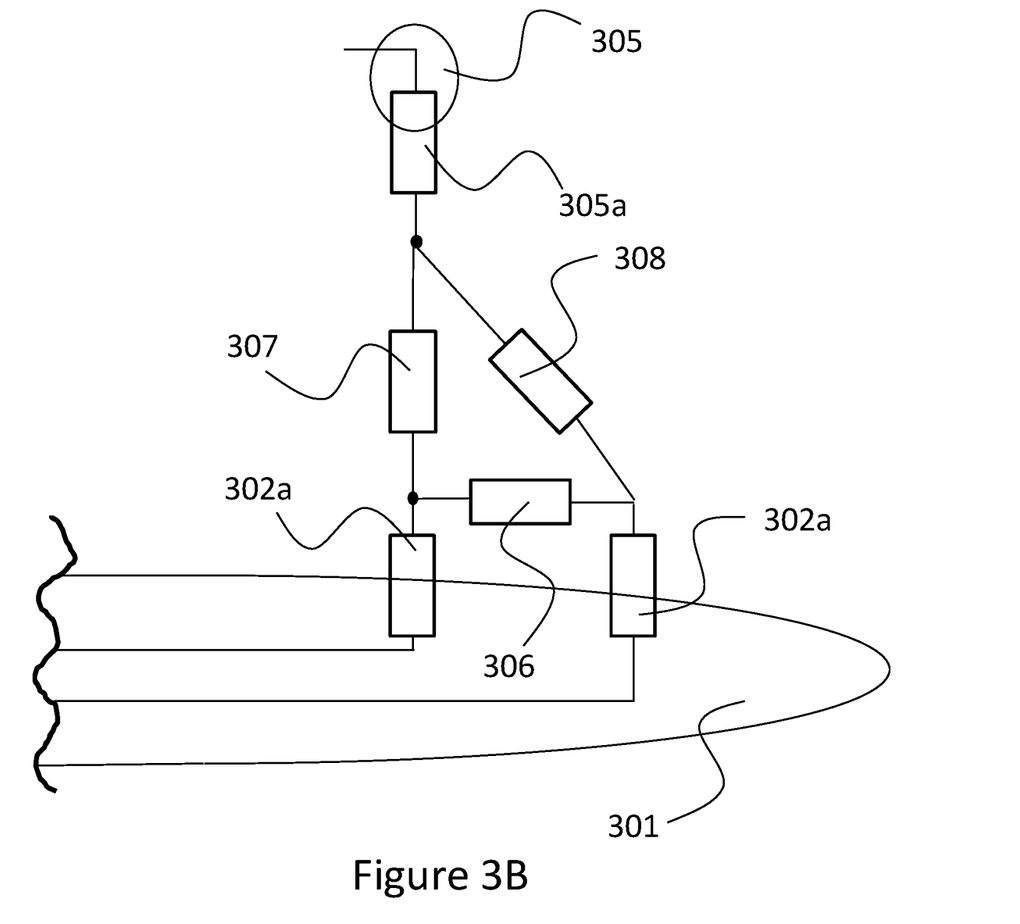

FIG. 3B shows an equivalent circuit of the example electrode lead shown in FIG. 3A. The impedances 302a and 305a refer to the electrode to tissue interface impedances of the electrode contact 302 and ground electrode 305 respectively. Impedances 307 and 308 refers to the tissue 304 impedances and lateral impedance 306 refers to the impedance between the two electrode contacts 302. Impedance field telemetry for example is well known in the field, may be used to measure and calculate the impedances, e.g. impedances 307 and 308. In a further embodiment of the invention, the functional relation between tissue heating and MRI electrode current signal may additionally depend on the tissue impedance, e.g. impedances 307 and 308. The dependence may be quadratic with the MRI electrode current signal and linear with the impedance. For example the measured MRI electrode current signal $I_w$ may be squared and multiplied by the impedance 307. In a further embodiment, the impedances 307 and 308 may be recalculated to form effective impedances by taking the lateral impedance 306 into account. These so calculated effective impedances are then used for calculation of the additional functional dependency from the tissue impedance. The smaller the lateral impedance 306, the lower the effective impedances will be, i.e. current spread in the tissue is spatially widened. This functional relation and including any further calibration coefficients may be determined during manufacturing in the same way as set out before.

Although various exemplary embodiments of the invention have been disclosed, it should be apparent to those skilled in the art that various changes and modifications can be made which will achieve some of the advantages of the invention without departing from the true scope of the invention.

What is claimed is:

1. A cochlear implant arrangement comprising:
    an implantable electrode lead containing a plurality of electrode wires each having a terminal end forming an electrode contact configured to deliver electrode stimulation signals carried by the electrode wires to adjacent auditory neural tissue for perception as sound by a patient;
    an implantable stimulator coupled to the electrode lead and configured to process an implant communications signal received from an external transmitter device to produce the electrode stimulation signals for the plurality of electrode wires;
    a magnetic resonance imaging (MRI) telemetry module coupled to the implantable stimulator and the electrode lead; and
    an MRI telemetry link configured to transmit an MRI telemetry signal from the MRI telemetry module to an external telemetry monitor;
    wherein the MRI telemetry module is configured to:
        i. measure MRI-induced electrode current in the electrode lead during an MRI process performed on the patient,
        ii. perform frequency shaping to compensate for influence of MRI frequency on the measured MRI-induced electrode current,
        iii. output to the external telemetry monitor the MRI telemetry signal based on the measured MRI-induced electrode current, and
        iv. determine a tissue temperature signal based on the MRI telemetry signal, as a function of the compensated MRI-induced electrode current, to indicate tissue heating occurring at the electrode contacts from the MRI process.

2. The cochlear implant arrangement according to claim 1, wherein the MRI telemetry module determines the MRI telemetry signal as a frequency dependent relationship between the measured MRI-induced electrode current and the tissue heating.

3. The cochlear implant arrangement according to claim 1, further comprising:
    an MRI telemetry memory coupled to the MRI telemetry module and configured to receive the MRI telemetry signal output from the MRI telemetry module for later delivery to the external telemetry sensor after conclusion of the MRI process.

4. The cochlear implant arrangement according to claim 1, wherein the MRI telemetry link is an optical link.

5. The cochlear implant arrangement according to claim 1, wherein the MRI telemetry link is a radiofrequency link.

6. The cochlear implant arrangement according to claim 1, wherein the MRI telemetry module is configured to measure MRI-induced electrode current on only one electrode wire.

7. The cochlear implant arrangement according to claim 1, wherein the MRI telemetry module is configured to measure MRI-induced electrode current on a plurality of electrode wires.

8. The cochlear implant arrangement according to claim 1, wherein the implantable stimulator includes electrode driver amplifiers configured to deliver the stimulation signals to the electrode wires, and wherein the MRI telemetry module is configured to measure MRI-induced electrode current based on a supply voltage generated for the electrode driver amplifiers during the MRI process.

9. A magnetic resonance imaging (MRI) telemetry process for a cochlear implant system, the process comprising:
measuring MRI-induced electrode current in a cochlear implant electrode lead during an MRI process performed on a patient,
performing frequency shaping to compensate for influence of MRI frequency on the measured MRI-induced electrode current,
outputting an MRI telemetry signal based on the measured MRI-induced electrode current for an external telemetry sensor, and
determining a tissue temperature signal based on the MRI telemetry signal, as a function of the compensated MRI-induced electrode current, to indicate tissue heating produced by the electrode lead during the MRI process.

10. The MRI telemetry process according to claim 9, wherein the MRI telemetry module determines the MRI telemetry signal as a frequency dependent relationship between the measured MRI-induced electrode current and the tissue heating.

11. The MRI telemetry process according to claim 9, wherein outputting the MRI telemetry signal for the external telemetry sensor occurs after conclusion of the MRI process.

12. The MRI telemetry process according to claim 9, wherein outputting the MRI telemetry signal for the external sensor occurs during the MRI process.

13. The MRI telemetry process according to claim 9, wherein an optical link is used for outputting the MRI telemetry signal.

14. The MRI telemetry process according to claim 9, a radiofrequency link is used for outputting the MRI telemetry signal.

15. The MRI telemetry process according to claim 9, wherein the MRI-induced electrode current is measured on only one electrode wire in the cochlear implant electrode lead.

16. The MRI telemetry process according to claim 9, wherein the MRI-induced electrode current is measured on a plurality of electrode wires in the cochlear implant electrode lead.

17. The MRI telemetry process according to claim 9, wherein measuring the MRI-induced electrode current is based on measuring a supply voltage generated for the electrode lead during the MRI process.

* * * * *